US008625872B2

(12) United States Patent
Ohishi

(10) Patent No.: US 8,625,872 B2
(45) Date of Patent: Jan. 7, 2014

(54) MEDICAL IMAGE PROCESSING APPARATUS AND MEDICAL IMAGE PROCESSING METHOD

(71) Applicants: Kabushiki Kaisha Toshiba, Tokyo (JP); Toshiba Medical Systems Corporation, Otawara (JP)

(72) Inventor: Satoru Ohishi, Otawara (JP)

(73) Assignees: Kabushiki Kaisha Toshiba, Tokyo (JP); Toshiba Medical Systems Corporation, Tochigi-ken (JP)

( * ) Notice: Subject to any disclaimer, the term of this patent is extended or adjusted under 35 U.S.C. 154(b) by 0 days.

(21) Appl. No.: 13/686,879

(22) Filed: Nov. 27, 2012

(65) Prior Publication Data

US 2013/0089251 A1 Apr. 11, 2013

Related U.S. Application Data

(63) Continuation of application No. 12/961,879, filed on Dec. 7, 2010, now Pat. No. 8,340,382.

(30) Foreign Application Priority Data

Dec. 7, 2009 (JP) .................................. 2009-277916
Nov. 5, 2010 (JP) .................................. 2010-248678

(51) Int. Cl.
*G06K 9/00* (2006.01)
*G01N 23/223* (2006.01)

(52) U.S. Cl.
USPC .............................. 382/131; 382/274; 378/46

(58) Field of Classification Search
USPC ......... 382/100, 106–107, 128–134, 154–155, 382/162, 168, 173, 181, 199, 232, 254, 274, 382/276, 291, 294, 305, 312; 378/6, 20, 21, 378/23, 25, 28, 46

See application file for complete search history.

(56) References Cited

U.S. PATENT DOCUMENTS 7,236,622 B2 * 6/2007 Chen et al. ..................... 382/132
7,778,453 B2 * 8/2010 Camus et al. .................. 382/128

(Continued)

FOREIGN PATENT DOCUMENTS

JP 2009-153870 A 7/2009

OTHER PUBLICATIONS

"C-Arm CT Measurement of Cerebral Blood Volume: An Experimental Study in Canines", AJNR Am. J. Neuroradiol., May 2009: 30, pp. 917-922.

*Primary Examiner* — Seyed Azarian
(74) *Attorney, Agent, or Firm* — Yoshida & Associates, LLC

(57) ABSTRACT

In a medical image processing apparatus according to an embodiment, an image inverting unit generates a first inverted image obtained by inverting a first medical image in a left-and-right direction of an examined subject and generates a second inverted image obtained by inverting a second medical image that is different from the first medical image in the left-and-right direction of the examined subject. A displacement detecting unit detects a displacement between the first medical image and the first inverted image. A registration unit generates, based on the displacement detected by the displacement detecting unit, a corrected image obtained by correcting the second medical image or a corrected inverted image obtained by correcting the second inverted image. A difference image generating unit generates a difference image between the second inverted image and the corrected image or a difference image between the second medical image and the corrected inverted image.

16 Claims, 5 Drawing Sheets

(56) References Cited

U.S. PATENT DOCUMENTS

| | | |
|---|---|---|
| 7,792,346 B2 * | 9/2010 | Lienard et al. ............... 382/130 |
| 8,081,812 B2 * | 12/2011 | Kreiser ........................ 382/132 |
| 2007/0036405 A1 * | 2/2007 | Lienard et al. ............... 382/128 |
| 2010/0215237 A1 * | 8/2010 | Ohishi ........................ 382/131 |

* cited by examiner

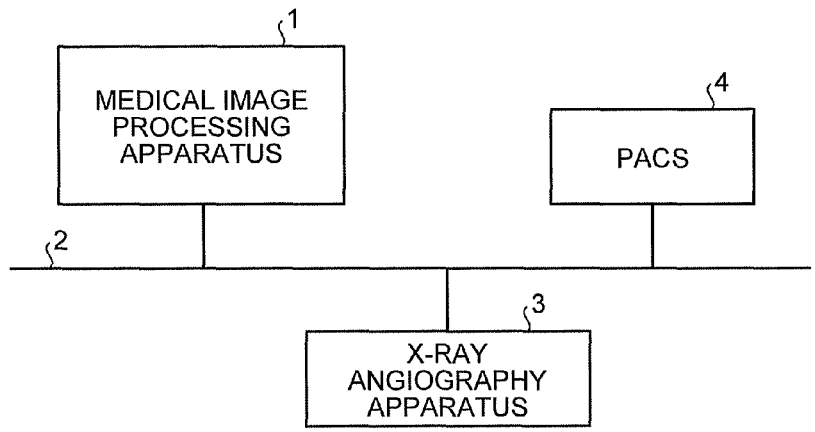
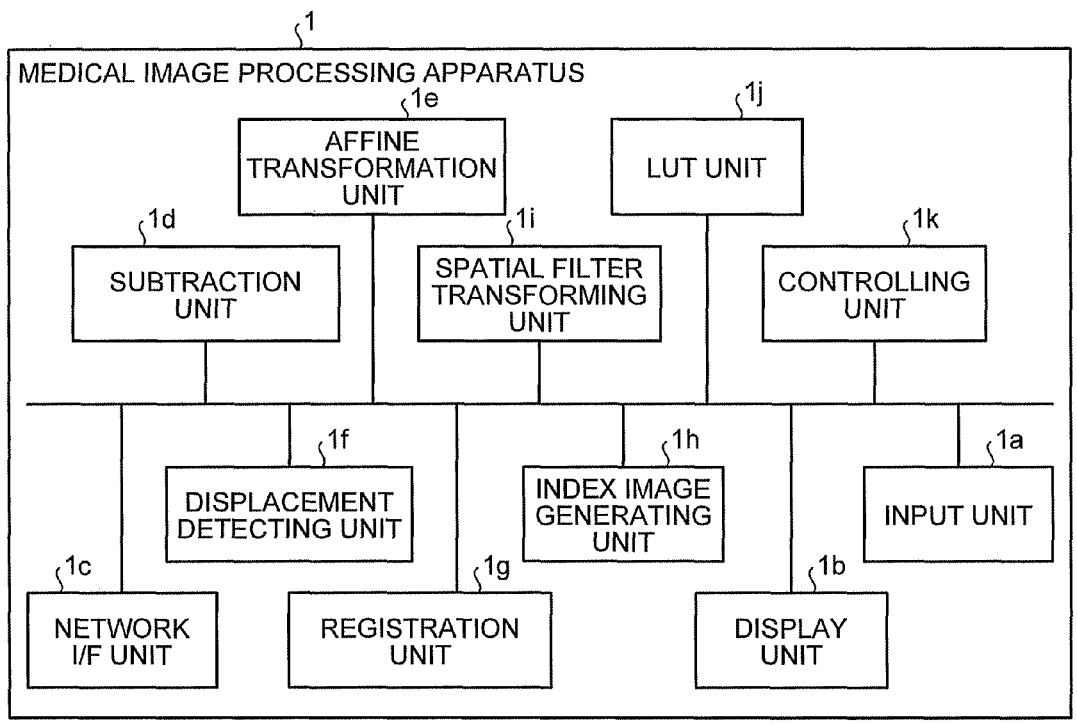

MEDICAL IMAGE PROCESSING APPARATUS AND MEDICAL IMAGE PROCESSING METHOD

CROSS-REFERENCE TO RELATED APPLICATIONS

This application is based upon and claims the benefit of priority from Japanese Patent Application No. 2009-277916, filed on Dec. 7, 20.09; and Japanese Patent Application No. 2010-248678, filed on Nov. 5, 2010, the entire contents of all of which are incorporated herein by reference.

FIELD

Embodiments described herein relate generally to a medical image processing apparatus and a medical image processing method.

BACKGROUND

Generally speaking, to make a diagnosis of a cerebral infarction, images that are obtained by performing, for example, Magnetic Resonance Imaging (MRI), Computed Tomography (CT), Single Photon Emission Computed Tomography (SPECT), and Positron Emission Tomography (PET) are used. Unless the circulation in an infarction site is resumed within three hours of an onset, the damage to the brain becomes significant, and part of the body functions of the patient may be lost or the brain damage may result in death.

One of the techniques that are known to be used for treating a lesion is to insert a catheter up to the lesion while viewing an X-ray transmission image. This technique is called an intervention. Examples of intervention treatments that can be applied to the blood vessels that have a direct impact on the head include a treatment by which a catheter is put through a stenosis site in the neck, before the balloon provided around the catheter is blown up so as to expand the stenosis site, and a treatment for a cerebral aneurysm by which a catheter is advanced to a closer end of the cerebral aneurysm, and the aneurysm is filled with a coil ejected from a tip of the catheter, so as to prevent the blood streams from entering the aneurysm. During these treatments, some of the plaques adhering to a blood clot or a stenosis site may flow toward the periphery and may block a peripheral blood vessel so as to cause a cerebral infarction. If such an infarction has occurred in a relatively large blood vessel, it is possible to recognize the occurrence of the infarction during a check-up imaging examination that is performed after the intervention treatment. However, in the case where an infarction has occurred in a small blood vessel, it is difficult, in many cases, to recognize the occurrence of the infarction during a check-up imaging examination. In those situations, according to a currently-used workflow, it is determined, whether an infarction has occurred by performing a CT examination, an MRI examination, or the like when three hours or one day has passed since the completion of the intervention treatment. According to this workflow, however, it is extremely difficult to resume the circulation in the infarction site within three hours of an onset.

To cope with this problem, a function has recently been proposed with which it is possible to check the manner in which blood is perfused by employing an X-ray angiography apparatus used for performing intervention treatments. When this function is used, images are taken while a C-arm is rotated around a patient at a high speed before and after a contrast media is injected into the patient. A three-dimensional image indicating an opacification degree of the contrast media is generated by reconstructing an image while using a subtraction image between the images taken before and after the injection of the contrast media, and also, a three-dimensional image indicating a body structure of the patient is generated from the image taken before the injection. After that, an area that has a CT value corresponding to the brain tissue is extracted from the three-dimensional image indicating the body structure. Further, by eliminating the areas other than the extracted area from the three-dimensional image indicating the opacification degree of the contract agent, it is possible to extract only the opacification degree of the contrast media in the brain tissue. There is a possibility that a part of the brain tissue that exhibits a low degree of opacification from the contrast media may be an infarction site. It is also possible to determine that the parts that exhibit a high degree of opacification from the contrast media have normal bloodstreams. It should be noted, however, that this imaging process is not supposed to be performed as a routine. Thus, the amount of contrast media used in the imaging process and the radiation exposure dose for the patient cause an additional burden upon the patient. In particular, according to this method, it is necessary to visualize the veins using a contrast media, the capillary vessels, and the arteries altogether, and the amount of the contrast media being used is very large.

BRIEF DESCRIPTION OF THE DRAWINGS

FIG. 1 is a diagram of an example of a medical image processing system according to a first embodiment;

FIG. 2 is a functional block diagram of a medical image processing apparatus according to the first embodiment;

DETAILED DESCRIPTION

Figure 3:
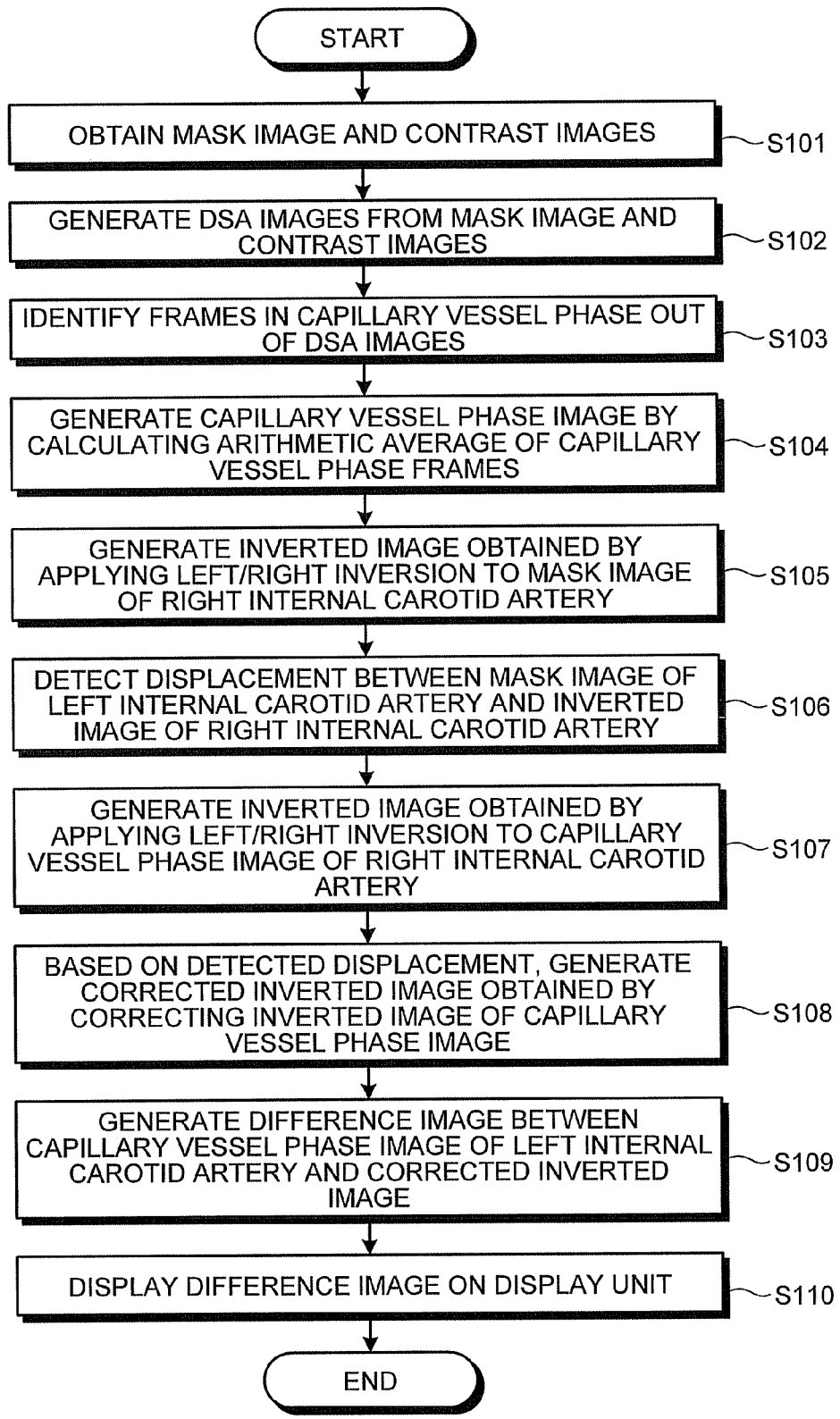
FIG. 3 is a flowchart of a process performed by the medical image processing apparatus according to the first embodiment.

A medical image processing apparatus according to an embodiment includes an image inverting unit, a displacement detecting unit, a registration unit, and a difference image generating unit. The image inverting unit generates a first inverted image obtained by inverting a first medical image in a left-and-right direction of an examined subject and generates a second inverted image obtained by inverting a second medical image that is different from the first medical image in the left-and-right direction of the examined subject. The displacement detecting unit detects a displacement between the first medical image and the first inverted image. The registration unit, based on the displacement that has been detected by the displacement detecting unit, generates one of a corrected image obtained by correcting the second medical image and a corrected inverted image obtained by correcting the second inverted image. The difference image generating unit generates one of a difference image between the second inverted image and the corrected image and a difference image between the second medical image and the corrected inverted image.

In the following sections, exemplary embodiments of a medical image processing apparatus and a medical image processing method will be explained in detail with reference to the accompanying drawings. However, embodiments of the medical image processing apparatus and the medical image processing method are not limited to the exemplary embodiments described below. In the exemplary embodiments described below, a medical image processing system that includes a medical image processing apparatus according to any of the exemplary embodiments and various types of medial image collecting apparatuses will be explained.

First, an example of a medical image processing system according to a first embodiment will be explained.

FIG. 1 is a diagram of the example of the medical image processing system according to the first embodiment. As shown in FIG. 1, a medical image processing apparatus 1 according to the first embodiment is connected to an X-ray angiography apparatus 3 and a Picture Archiving and Communication System (PACS) 4 via a network 2.

FIG. 2 is a functional block diagram of the medical image processing apparatus 1 according to the first embodiment. As shown in FIG. 2, the medical image processing apparatus 1 includes an input unit 1a, a display unit 1b, a network interface (I/F) unit 1c, a subtraction unit 1d, an affine transformation unit 1e, a displacement detecting unit 1f, a registration unit 1g, an index image generating unit 1h, a spatial filter transforming unit 1i, a Look-Up Table (LUT) unit 1j, and a controlling unit 1k.

The input unit 1a receives various types of operations performed on the medical image processing apparatus 1 from an operator thereof. For example, the input unit 1a may be configured with any of the following: a mouse, a keyboard, a trackball, and a pointing device.

The display unit 1b displays various types of images that have been processed by the medical image processing apparatus 1 and various types of information such as a Graphical User Interface (GUI). For example, the display unit 1b may be configured with a Cathode Ray Tube (CRT) monitor or a liquid crystal display monitor.

The network I/F unit 1c controls transmissions and receptions of various types of information that are transmitted or received via the network 2. The network I/F unit 1c obtains a medical image that has been taken by the X-ray angiography apparatus 3.

The subtraction unit 1d generates a difference image such as a Digital Subtraction Angiography (DSA) image. For example, the subtraction unit 1d generates a DSA image from the medical image that has been obtained by the network I/F unit 1c.

The affine transformation unit 1e enlarges or reduces the size of images, and moves and inverts images. For example, the affine transformation unit 1e generates an inverted image by applying a left/right inversion to the medical image that has been obtained by the network I/F unit 1c.

The displacement detecting unit 1f detects a displacement between the medical image that has been obtained by the network I/F unit 1c and the inverted image that has been generated by the affine transformation unit 1e.

The registration unit 1g corrects the medical image based on the displacement that has been detected by the displacement detecting unit 1f. For example, based on the displacement that has been detected by the displacement detecting unit 1f, the registration unit 1g generates a corrected original image obtained by correcting the medical image that has been obtained by the network I/F unit 1c and generates a corrected inverted image obtained by correcting the inverted image that has been generated by the affine transformation unit 1e.

The index image generating unit 1h generates an index image that serves as an index indicating the bloodstreams. For example, the index image generating unit 1h generates, as an index image, a difference image between the medical image that has been obtained by the network I/F unit 1c and the corrected inverted image that has been generated by the registration unit 1g.

The spatial filter transforming unit 1i performs, for example, a frequency emphasizing process or a low-pass filtering process on an image. The Look-Up Table (LUT) unit 1j transforms the gray level of an image.

The controlling unit 1k controls various types of processing that are performed by the medical image processing apparatus 1. For example, the controlling unit 1k moves the control from one of the functional units included in the medical image processing apparatus 1 to another one of the functional units, and also, forwards data from one of the functional units to another one of the functional units.

Next, a flow in a process performed in the medical image processing system according to the first embodiment will be explained more specifically. In the following sections, an example in which the head of a subject is examined by using the X-ray angiography apparatus 3 will be explained.

During a head examining process performed by using an X-ray angiography apparatus, diagnoses are primarily made regarding the shapes of the blood vessels such as cerebral aneurysms, stenoses, and anomalies as well as regarding the bloodstreams. Generally speaking, a diagnosis of a cerebral infarction, which is caused when one or more of the capillary vessels in the brain have an infarction, is made by using an X-ray CT apparatus or an MRI apparatus, because it is not possible to recognize the capillary vessels by using an X-ray angiography apparatus.

For example, examples of treatments of the head using an X-ray angiography apparatus include a treatment by which a catheter is inserted up to a stenosis site and a balloon provided around the catheter is blown up so as to expand the stenosis site. This treatment is called an intervention. During an intervention, when the balloon is blown up, there is a possibility that some of the plaques in the stenosis site may move to the peripheries, and the plaques may cause an infarction in the capillary vessels in the brain. In that situation, the infarction is discovered when an examination is performed by using an X-ray CT apparatus, after the intervention has been finished.

Normally, however, it takes at least approximately three hours or even about one day in some cases, before the examination is performed by using an X-ray CT apparatus, after an intervention has been finished. If it is possible to treat infarctions in a short period of time, there will be hardly any damage to the brain; however, the longer period of time it takes, the lower the rate of recovery becomes. In particular, the rate of recovery drastically drops after three hours. Thus, to improve the Quality of Life (QOL) of patients, it is desirable to be able to check on infarctions while an intervention is being performed or at the end of intervention.

According to the first embodiment, it becomes possible to diagnose a cerebral infarction caused by an infarction of the capillary vessels, which has not conventionally been diagnosable by using an X-ray angiography apparatus. In the following sections, a method therefor will be specifically explained.

First, a process performed by the X-ray angiography apparatus 3 will be explained.

Normally, when a treatment procedure has been completed, four blood vessels that are the major blood vessels in the brain are visualized using a contrast media and images thereof are taken, so as to make a diagnosis to determine whether an infarction has occurred in each of the four blood vessels. In this situation, the four blood vessels are the right internal carotid artery, the left internal carotid artery, the right vertebral artery, and the left vertebral artery. The right internal carotid artery nourishes the frontal part, the temporal part, and the parietal part of the right brain. The left internal carotid artery nourishes the frontal part, the temporal part, and the parietal part of the left brain. The right vertebral artery and the left vertebral artery nourish the base part and the occipital part of the brain.

While visualizing using a contrast media the right internal carotid artery, the left internal carotid artery, the right vertebral artery, and the left vertebral artery, the X-ray angiography apparatus 3 generates a DSA image of each of these blood vessels. More specifically, the X-ray angiography apparatus 3 generates an average image of the images corresponding to a plurality of frames that are taken before the vessels are visualized using a contrast media, as a mask image. Further, the X-ray angiography apparatus 3 sequentially takes contrast images while a contrast media is flowing through the blood vessels.

After that, the X-ray angiography apparatus 3 generates the DSA images by subtracting the mask image from each of the frames of the contrast images that have been taken. For example, the X-ray angiography apparatus 3 generates each of the DSA images by using Expression (1) shown below:

$$DSA_n(i, j) = \log_e \frac{mask(i, j)}{constrast_n(i, j)} \quad (1)$$

In Expression (1), (i,j) denotes coordinates in the image. "$DSA_n(i,j)$" denotes a DSA image in an n'th frame, whereas "$contrast_n(i,j)$" denotes a contrast image in an n'th frame. Further, "mask(i,j) denotes a mask image.

When having generated the DSA images, the X-ray angiography apparatus 3 displays the generated DSA images on the display unit. Also, the X-ray angiography apparatus 3 transfers the mask image and all the contrast images to the medical image processing apparatus 1 via the network 2. In this situation, the X-ray angiography apparatus 3 transfers the mask image and the contrast images of each of the arteries, i.e., the right internal carotid artery, the left internal carotid artery, the right vertebral artery, and the left vertebral artery to the medical image processing apparatus 1.

The X-ray angiography apparatus 3 may transfer the angiography examination images according to an instruction from an operator or may transfer all the angiography examination images automatically. Alternatively, for example, an arrangement is acceptable in which an analysis described herein is optional at acquisition program in the X-ray angiography apparatus 3 in advance so that, only when the acquisition program which has the option has been selected by an operator, the X-ray angiography apparatus 3 transfers the angiography examination images to the medical image processing apparatus 1.

Next, a process performed by the medical image processing apparatus 1 will be explained.

FIG. 3 is a flowchart of a process performed by the medical image processing apparatus 1 according to the first embodiment. As shown in FIG. 3, the medical image processing apparatus 1 is configured so that the network I/F unit 1c obtains mask images each of which is expressed as mask(i,j) and contrast images that are expressed as $contrast_n(i,j)$ that have been transferred from the X-ray angiography apparatus 3 (step S101).

In this situation, the network I/F unit 1c obtains mask(i,j) and $contrast_n(i,j)$ of each of the following arteries: the right internal carotid artery, the left internal carotid artery, the right vertebral artery, and the left vertebral artery. Further, the network I/F unit 1c stores the mask images and the contrast images that have been received into a storage unit (not shown).

After that, the subtraction unit 1d reads mask(i,j) and $contrast_n(i,j)$ from the storage unit and generates DSA images from mask(i,j) and $contrast_n(i,j)$ that have been read (step S102).

In this situation, for example, the subtraction unit 1d generates the images expressed as $DSA_n(i,j)$ for each of the blood vessels by using Expression (1), in the same manner as the X-ray angiography apparatus 3 does. The $DSA_n(i,j)$ images can be roughly classified into three types of temporal phases. The first temporal phase is an artery phase in which the arteries are dominant; the following temporal phase is a capillary vessel phase in which the capillary vessels are dominant, while the entirety of the brain cells are opacified, and there is hardly any influence of the arteries and the veins; and the last temporal phase is a vein phase in which the veins are dominant.

Subsequently, after having generated $DSA_n(i,j)$ for each of the blood vessels, the subtraction unit 1d identifies frames that are in the capillary vessel phase, out of the $DSA_n(i,j)$ images that have been generated (step S103). In this situation, for example, the subtraction unit 1d receives a selecting operation to select the capillary vessel phase frames from the operator via the input unit 1a and identifies the capillary vessel phase frames based on the received selecting operation.

After that, the subtraction unit 1d generates a capillary vessel phase image by calculating the arithmetic average of the capillary vessel phase frames that have been identified (step S104). In this situation, for example, the subtraction unit 1d generates the capillary vessel phase image by using Expression (2) shown below:

$$DSA(i, j) = \frac{\sum_{n=N1}^{N2} DSA_n(i, j)}{(N2 - N1 + 1)} \quad (2)$$

In Expression (2), N1 and N2 denote the frames at the beginning and at the end of the capillary vessel phase, respectively.

It should be noted that the subtraction unit 1d generates the capillary vessel phase image described above for each of the vessels. For example, the subtraction unit 1d generates a capillary vessel phase image of the right internal carotid artery expressed as $DSA_{RICA}(i,j)$ and a capillary vessel phase image of the left internal carotid artery expressed as $DSA_{LICA}(i,j)$. The subtraction unit 1d then stores the capillary vessel phase images that have been generated into the storage unit.

Subsequently, the affine transformation unit 1e reads the mask image of the right internal carotid artery expressed as $mask_{RICA}(i,j)$ and the mask image of the left internal carotid artery expressed as $mask_{LICA}(i,j)$ from the storage unit. After that, the affine transformation unit 1e generates an inverted image expressed as $Rmask_{RICA}(i,j)$ obtained by applying a left/right inversion to $mask_{RICA}(i,j)$ that has been read (step S105). Subsequently, the affine transformation unit 1e stores the generated inverted image expressed as $Rmask_{RICA}(i,j)$ into the storage unit. Further, the affine transformation unit 1e forwards mask$_{LICA}$(i,j) and Rmask$_{RICA}$(i,j) to the displacement detecting unit 1f.

Subsequently, the displacement detecting unit 1f detects a displacement between mask$_{LICA}$(i,j) and Rmask$_{RICA}$(i,j) that have been forwarded from the affine transformation unit 1e (step S106). For example, the displacement detecting unit 1f detects the displacement between mask$_{LICA}$(i,j) and Rmask$_{RICA}$(i,j) by using Expression (3) shown below:

$$MR(\Delta i, \Delta j) = \sum_{i=1}^{N}\sum_{j=1}^{N}\{mask_{LICA}(i,j) - \alpha Rmask_{RICA}(i-\Delta i, j-\Delta j)\}^2 \quad (3)$$

In Expression (3), MR($\Delta i,\Delta j$) denotes a degree of divergence between mask$_{LICA}$(i,j) and $\alpha$Rmask$_{RICA}$(i-$\Delta i$,j-$\Delta j$). Further, $\alpha$ denotes a correcting coefficient used for correcting changes in the luminance caused by the conditions under which the images have been taken, between the image of the right internal carotid artery and the image of the left internal carotid artery. Further, N denotes the image size.

The displacement detecting unit 1f searches for such a value of ($\Delta i,\Delta j$) that makes the value of MR($\Delta i,\Delta j$) smallest, while varying the value of ($\Delta i,\Delta j$) by using an iterative algorithm. After that, the displacement detecting unit 1f forwards the value of ($\Delta i,\Delta j$) that has been found in the search to the registration unit 1g, as a displacement expressed as ($\Delta i_0,\Delta j_0$). In the present example, to simplify the explanation, a situation in which the displacement in a two-dimensional direction is detected is explained; however, it is desirable to further detect a displacement in a rotational direction.

Subsequently, the affine transformation unit 1e reads the capillary vessel phase image of the right internal carotid artery expressed as DSA$_{RICA}$(i,j) from the storage unit and generates an inverted image expressed as RDSA$_{RICA}$(i,j) obtained by applying a left/right inversion to DSA$_{RICA}$(i,j) that has been read (step S107). After that, the affine transformation unit 1e stores RDSA$_{RICA}$(i,j) that has been generated into the storage unit.

Subsequently, the registration unit 1g reads RDSA$_{RICA}$(i,j) from the storage unit. Further, the registration unit 1g generates a corrected inverted image expressed as RDSA$_{RICA}$(i-$\Delta i_0$,j-$\Delta j_0$) obtained by correcting RDSA$_{RICA}$(i,j), based on the displacement expressed as ($\Delta i_0,\Delta j_0$) that has been forwarded from the displacement detecting unit 1f (step S108). After that, the registration unit 1g forwards RDSA$_{RICA}$(i-$\Delta i_0$, j-$\Delta j_0$) that has been generated to the index image generating unit 1h.

Subsequently, the index image generating unit 1h reads the capillary vessel phase image of the left internal carotid artery expressed as DSA$_{LICA}$(i,j) from the storage unit. After that, the index image generating unit 1h generates a difference image between DSA$_{LICA}$(i,j) that has been read and RDSA$_{RICA}$(i-$\Delta i_0$,j-$\Delta j_0$) that has been forwarded from the registration unit 1g, as an index image indicating an index for the bloodstreams (step S109).

For example, the index image generating unit 1h generates a difference image expressed as PF$_{LICA\text{-}RICA}$(i,j) by subtracting RDSA$_{RICA}$(i-$\Delta i_0$,j-$\Delta j_0$) from DSA$_{LiCA}$(i,j) as shown in Expression (4) below:

$$PF_{LICA\text{-}RICA}(i,j) = DSA_{LICA}(i,j) - RDSA_{RICA}(i-\Delta i_0, j-\Delta j_0) \quad (4)$$

After that, the index image generating unit 1h displays PF$_{LICA\text{-}RICA}$(i,j) that has been generated on the display unit 1b (step S110). In this situation, the index image generating unit 1h may display PF$_{LICA\text{-}RICA}$(i,j) as a black-and-white image or as a color image.

For example, in the case where there is no infarction site at all, the bloodstreams on the left and on the right are substantially the same as each other. Thus, the index image is an image that is substantially uniform throughout the image. In other words, the pixel value of each of all the pixels in PF$_{LICA\text{-}RICA}$(i,j) is "0". In contrast, in the case where an infarction has occurred in the right internal carotid artery system, a high positive signal is detected in a region that is positioned bilaterally symmetric to the infarction site, within PF$_{LICA\text{-}RICA}$(i,j).

As explained above, according to the first embodiment, for example, the affine transformation unit 1e generates the inverted image expressed as Rmask$_{RICA}$(i,j) obtained by applying a left/right inversion to the mask image of the right internal carotid artery expressed as mask$_{RICA}$(i,j) and generates the inverted image expressed as RDSA$_{RICA}$(i,j) obtained by applying a left/right inversion to the capillary vessel phase image of the right internal carotid artery expressed as DSA$_{RICA}$(i,j). Further, the displacement detecting unit 1f detects the displacement between the mask image of the left internal carotid artery expressed as mask$_{LICA}$(i,j) and the inverted image expressed as Rmask$_{RICA}$(i,j) that has been generated by the affine transformation unit 1e. Further, the registration unit 1g generates the corrected inverted image expressed as RDSA$_{RICA}$(i-$\Delta i_0$,j-$\Delta j_0$) obtained by correcting the inverted image expressed as RDSA$_{RICA}$(i,j), based on the detected displacement expressed as ($\Delta i_0,\Delta j_0$). After that, the index image generating unit 1h generates the difference image expressed as PF$_{LICA\text{-}RICA}$(i,j) between the capillary vessel phase image of the left internal carotid artery expressed as DSA$_{LICA}$(i,j) and the corrected inverted image expressed as RDSA$_{RICA}$(i-$\Delta i_0$,j-$\Delta j_0$), as the index image indicating an index for the bloodstreams.

Alternatively, another arrangement is acceptable in which the registration unit 1g generates a corrected image expressed as DSA$_{LICA}$(i+$\Delta i_0$,j+$\Delta j_0$) obtained by correcting the capillary Vessel phase image of the left internal carotid artery expressed as DSA$_{LICA}$(i,j), based on the displacement expressed as ($\Delta i_0,\Delta j_0$) that has been detected by the displacement detecting unit 1f. In that situation, the index image generating unit 1h generates, as an index image indicating an index for the bloodstreams, a difference image between the corrected image expressed as DSA$_{LICA}$(i+$\Delta j_0$,j+$\Delta j_0$) and the inverted image expressed as RDSA$_{RICA}$(i,j), as PF$_{LICA\text{-}RICA}$ (i,j).

With the configuration described above, in the case where an infarction site has occurred in the right internal carotid artery system, the infarction site is shown with an emphasis in the difference image expressed as PF$_{LICA\text{-}RICA}$(i,j). Consequently, it is possible to present, with a high level of precision, a lesion area of the examined subject within the medical images.

In the exemplary embodiment described above, the example is explained in which the subtraction unit 1d identifies the frames that are in the capillary vessel phase, based on the selecting operation performed by the operator; however, the embodiment is not limited to this example. For example, another arrangement is acceptable in which the subtraction unit 1d automatically identifies the frames that are in the capillary vessel phase, without receiving the selecting operation from the operator.

Normally, in the case where the injection period of a contrast media is 2 seconds, a large part of an artery is visualized within approximately 0.5 seconds from the start of the injection of the contrast media. For this reason, the subtraction unit 1d generates an arithmetic average image of the frames that are taken between 0.5 seconds later and 2.5 seconds later and extracts an artery part by performing threshold value processing on the generated arithmetic average image. Further, the subtraction unit 1d generates an arithmetic average image of the frames that are taken between 2 seconds earlier than the completion of an image-taking process and the completion time of the image-taking process. The subtraction unit 1d then extracts a vein part by performing threshold value processing on the generated arithmetic average image.

After that, the subtraction unit 1d sets an area having a predetermined size around the center of the image as a Region Of Interest (ROI) and identifies the area within the ROI that is neither the artery part nor the vein part as a capillary vessel part. For example, an arrangement is acceptable in which the subtraction unit 1d has stored in advance, in a storage unit, information indicating an appropriate ROI for each of different Fields Of View (FOVS) (i.e., sizes of the viewing fields), so that the subtraction unit 1d can set the ROI based on the stored information.

After the capillary vessel part has been identified in this manner, the subtraction unit 1d generates profiles for the area of the artery part, for the area of the vein part, and for the area of the capillary vessel part that are contained in DSA (i,j).

Figure 4:
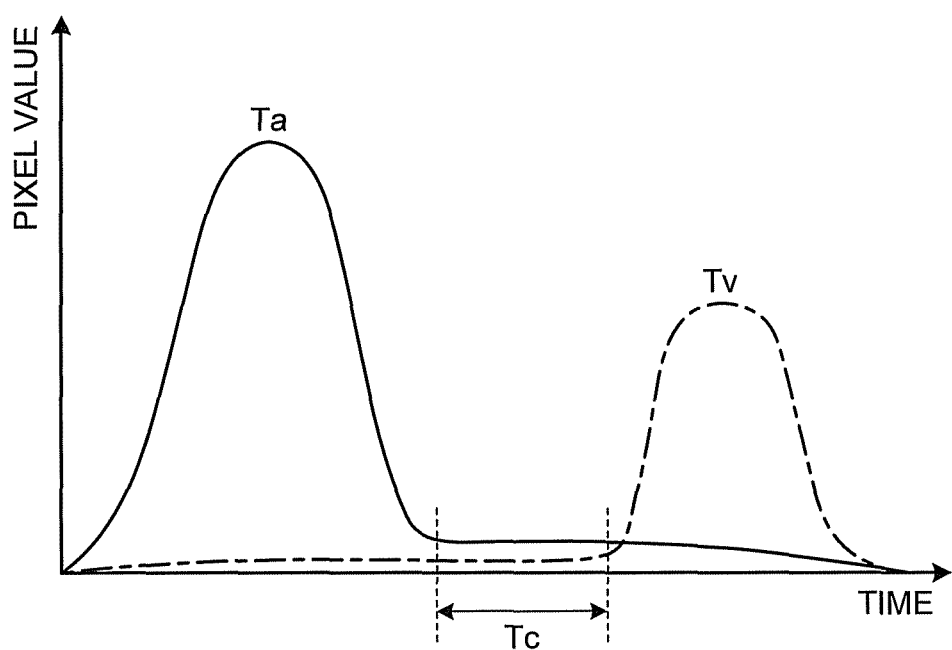
FIG. 4 is a chart depicting profiles of an area of an artery part and an area of a vein part that have been generated by a subtraction unit according to the first embodiment.

FIG. 4 is a chart depicting the profiles of the area of the artery part and the area of the vein part that have been generated by the subtraction unit 1d according to the first embodiment. In FIG. 4, the curve drawn with a solid line indicates the profile of the area of the artery part, whereas the curve drawn with a dashed line indicates the profile of the area of the vein part. Also, in FIG. 4, Ta denotes an artery phase, whereas Tv denotes a vein phase. As shown in FIG. 4, in the profile of the area of the artery part, the pixel value increases in the artery phase, while no change is observed in the pixel value when the artery phase is over. In the profile of the area of the vein part, no change is observed in the pixel value for a certain period of time after the image taking process is started, although the pixel value subsequently increases in the vein phase.

Accordingly, for example, the subtraction unit 1d detects such a temporal phase within the profile of the area of the artery part where no change is observed after the pixel value has increased. Also, the subtraction unit 1d detects such a temporal phase within the profile of the area of the vein part where the pixel value increases. After that, the subtraction unit 1d sets the range between the two detected temporal phases as a capillary vessel phase Tc and identifies the frames corresponding to the capillary vessel phase Tc that has been set, as the frames that are in the capillary vessel phase.

Further, in the description of the first embodiment above, the example is explained in which the index image generating unit 1h generates, as shown in Expression (4), the difference image expressed as $PF_{LICA-RICA}(i,j)$ by subtracting the inverted image expressed as $RDSA_{RICA}(i-\Delta i_0, j-\Delta j_0)$ that has been obtained by applying a left/right inversion to the capillary vessel phase image of the right internal carotid artery from the capillary vessel phase image of the left internal carotid artery expressed as $DSA_{LICA}(i,j)$; however, the embodiment is not limited to this example.

Alternatively, another arrangement is acceptable in which, for example, the index image generating unit 1h generates a difference image expressed as $PF_{RICA-LICA}(i,j)$ by subtracting the inverted image expressed as $RDSA_{LICA}(i-\Delta i_0, j+\Delta j_0)$ that has been obtained by applying a left/right inversion to the capillary vessel phase image of the left internal carotid artery from the capillary vessel phase image of the right internal carotid artery expressed as $DSA_{RICA}(i,j)$. In the $PF_{RICA-LICA}(i,j)$ image, in the case where an infarction has occurred in the right internal carotid artery system, a high negative signal is detected in the infarction site.

In addition, it is also possible to obtain, for example, an index for the bloodstreams in the vertebral artery system. In that situation, the subtraction unit 1d generates a capillary vessel phase image of the right vertebral artery expressed as $DSA_{RVA}(i,j)$ and a capillary vessel phase image of the left vertebral artery expressed as $DSA_{LVA}(i,j)$.

Subsequently, the affine transformation unit 1e reads a mask image of the right vertebral artery expressed as $mask_{RVA}(i,j)$ and a mask image of the left vertebral artery expressed as $mask_{RVA}(i,j)$ from the storage unit. Further, the affine transformation unit 1e generates an inverted image expressed as $Rmask_{RVA}(i,j)$ that is obtained by applying a left/right inversion to $mask_{RVA}(i,j)$. After that, the affine transformation unit 1e forwards $mask_{LVA}(i,j)$ and $Rmask_{RVA}(i,j)$ to the displacement detecting unit 1f.

Subsequently, the displacement detecting unit 1f detects a displacement between $mask_{LVA}(i,j)$ and $Rmask_{RVA}(i,j)$ that have been forwarded from the affine transformation unit 1e. For example, the displacement detecting unit 1f detects the displacement between $mask_{LVA}(i,j)$ and $Rmask_{RVA}(i,j)$ by using Expression (5) shown below:

$$MR(\Delta i, \Delta j) = \sum_{i=1}^{N}\sum_{j=1}^{N} \{mask_{LVA}(i,j) - \alpha Rmask_{RVA}(i-\Delta i, j-\Delta j)\}^2 \quad (5)$$

In Expression (5), $MR(\Delta i, \Delta j)$ denotes a degree of divergence between $mask_{LVA}(i,j)$ and $\alpha Rmask_{RVA}(i-\Delta i, j-\Delta i)$. Further, $\alpha$ denotes a correcting coefficient used for correcting changes in the luminance caused by the conditions under which the images have been taken, between the image of the right vertebral artery and the image of the left vertebral artery. Further, N denotes the image size.

The displacement detecting unit 1f searches for such a value of $(\Delta i, \Delta j)$ that makes the value of $MR(\Delta i, \Delta j)$ smallest, while varying the value of $(\Delta i, \Delta j)$ by using an iterative algorithm. After that, the displacement detecting unit 1f forwards the value of $(\Delta i, \Delta j)$ that has been found in the search to the registration unit 1g, as the displacement expressed as $(\Delta i_0, \Delta j_0)$.

Subsequently, the affine transformation unit 1e reads the capillary vessel phase image of the right vertebral artery expressed as $DSA_{RVA}(i,j)$ from the storage unit and generates an inverted image expressed as $RDSA_{RVA}(i,j)$ obtained by applying a left/right inversion to $DSA_{RVA}(i,j)$ that has been read. After that, the affine transformation unit 1e stores $RDSA_{RVA}(i,j)$ that has been generated into the storage unit.

Subsequently, the registration unit 1g reads $RDSA_{RVA}(i,j)$ from the storage unit. Further, the registration unit 1g generates a corrected inverted image expressed as $RDSA_{RVA}(i-\Delta i_0, j-\Delta j_0)$ obtained by correcting $RDSA_{RVA}(i,j)$, based on the displacement expressed as $(\Delta i_0, \Delta j_0)$ that has been forwarded from the displacement detecting unit 1f. After that, the registration unit 1g forwards $RDSA_{RVA}(i-\Delta i_0, j-\Delta j_0)$ that has been generated to the index image generating unit 1h.

Subsequently, the index image generating unit 1h reads the capillary vessel phase image of the left vertebral artery expressed as $DSA_{LVA}(i,j)$ from the storage unit. After that, the index image generating unit 1h generates a difference image between $DSA_{LVA}(i,j)$ that has been read and $RDSA_{RVA}(i-\Delta i_0,$ $j-\Delta j_0$) that has been forwarded from the registration unit $1g$, as an index image indicating an index for the bloodstreams.

For example, the index image generating unit $1h$ generates a difference image expressed as $PF_{LVA-RVA}(i,j)$ by subtracting $RDSA_{RVA}(i-\Delta i_0, j-\Delta j_0)$ from $DSA_{LVA}(i,j)$ as shown in Expression (6) below:

$$PF_{LVA-RVA}(i,j)=DSA_{LVA}(i,j)-RDSA_{RVA}(i-\Delta i_0, j-\Delta j_0) \quad (6)$$

Alternatively, another arrangement is acceptable in which, for example, the index image generating unit $1h$ generates a difference image expressed as $PF_{RVA-LVA}(i,j)$ by subtracting an inverted image expressed as $RDSA_{LVA}(i-\Delta i_0, j+\Delta j_0)$ that has been obtained by applying a left/right inversion to the capillary vessel phase image of the left vertebral artery from the capillary vessel phase image of the right vertebral artery expressed as $DSA_{RVA}(i,j)$.

The combinations of the images and the effects of the index images that have been explained above can be summarized as shown in Table 1 below. In Table 1, the images in the "mask" column and the images in the "Rmask" column are used by the displacement detecting unit $1f$ to detect the displacements. Further, either the image in the "DSA" column or the image in the "RDSA" column is corrected by the registration unit $1g$. The images shown in the "DSA" column and the images shown in the "RDSA" column are used by the index image generating unit $1h$ to generate the difference images. These images are obtained during a check-up imaging process that is performed on the blood vessels as a routine, after the treatment has been completed. Consequently, the burdens on the patients that are caused by contrast medias or radiation exposure doses do not increase.

In that situation, for example, the affine transformation unit $1e$ generates the inverted image expressed as $Rmask_{RVA}(i,j)$ by applying a left/right inversion to the mask image of the right vertebral artery expressed as $mask_{RVA}(i,j)$. After that, the displacement detecting unit $1f$ detects the displacement expressed as $(\Delta i_0, \Delta j_0)$ between $mask_{RVA}(i,j)$ and $Rmask_{RVA}(i,j)$.

Subsequently, the affine transformation unit $1e$ generates the inverted image $RDSA_{RVA}(i,j)$ obtained by applying a left/right inversion to the capillary vessel phase image of the right vertebral artery expressed as $DSA_{RVA}(i,j)$. Further, the registration unit $1g$ generates a corrected inverted image expressed as $RDSA_{RVA}(i-\Delta i_0, j-\Delta j_0)$ obtained by correcting $RDSA_{RVA}(i,j)$, based on the displacement expressed as $(\Delta i_0, \Delta j_0)$ that has been detected by the displacement detecting unit $1f$.

After that, the index image generating unit $1h$ generates a difference image between the capillary vessel phase image of the right vertebral artery expressed as $DSA_{RVA}(i,j)$ and $RDSA_{RVA}(i-\Delta i_0, j-\Delta j_0)$ that has been generated by the registration unit $1g$. For example, the index image generating unit $1h$ generates a difference image expressed as $PF_{RVA}(i,j)$ between the capillary vessel phase image of the right vertebral artery expressed as $DSA_{RVA}(i,j)$ and $RDSA_{RVA}(i-\Delta i_0, j-\Delta j_0)$ that has been generated by the registration unit $1g$, by using Expression (7) shown below:

$$PF_{RVA}(i,j)=DSA_{RVA}(i,j)-RDSA_{RVA}(i-\Delta i_0, j-\Delta j_0) \quad (7)$$

The pixel values of $PF_{RVA}(i,j)$ and $PF_{LICA-RICA}(i,j)$ are each expected to be an extremely small value and are therefore susceptible to impacts of noises. To cope with this situation, an arrangement is acceptable in which, for example, the spa-

TABLE 1

| PF | mask | Rmask | DSA | RDSA | Effects |
|---|---|---|---|---|---|
| $PF_{LICA-RICA}(i,j)$ | $mask_{LICA}(i,j)$ | $Rmask_{RICA}(i,j)$ | $DSA_{LICA}(i,j)$ | $RDSA_{RICA}(i,j)$ | The difference in the bloodstreams in the right brain through the right internal carotid artery system, from the bloodstreams in the left brain through the left internal carotid artery system |
| $PF_{RICA-LICA}(i,j)$ | $mask_{RICA}(i,j)$ | $Rmask_{LICA}(i,j)$ | $DSA_{RICA}(i,j)$ | $RDSA_{LICA}(i,j)$ | The difference in the bloodstreams in the left brain through the left internal carotid artery system, from the bloodstreams in the right brain through the right internal carotid artery system |
| $PF_{LVA-RVA}(i,j)$ | $mask_{LVA}(i,j)$ | $Rmask_{RVA}(i,j)$ | $DSA_{LVA}(i,j)$ | $RDSA_{RVA}(i,j)$ | The difference in the bloodstreams in the left and right brains through the right vertebral artery system, from the bloodstreams in the left and right brains through the left vertebral artery system |
| $PF_{RVA-LVA}(i,j)$ | $mask_{RVA}(i,j)$ | $Rmask_{LVA}(i,j)$ | $DSA_{RVA}(i,j)$ | $RDSA_{LVA}(i,j)$ | The difference in the bloodstreams in the left and right brains through the left vertebral artery system, from the bloodstreams in the left and right brains through the right vertebral artery system |

The left and the right vertebral arteries supply blood to the left brain and to the right brain at the same time. For this reason, another arrangement is acceptable in which, for example, an index image for the bloodstreams is generated only from one of the images i.e., either an image of the right vertebral artery or an image of the left vertebral artery, instead of using both of the images.

tial filter transforming unit $1i$ applies a spatial smoothing filter to $PF_{RVA}(i,j)$. With this arrangement, it is possible to eliminate, from $PF_{RVA}(i,j)$, noises that may be a cause of obstruction to diagnoses.

Alternatively, by using the same method as described above, another arrangement is acceptable in which, for example, the index image generating unit $1h$ generates a difference image expressed as $PF_{LVA}(i,j)$ by subtracting the inverted image expressed as $RDSA_{LVA}(i-\Delta i_0, j-\Delta j_0)$ that has been obtained by applying a left/right inversion to the capillary vessel phase image of the left vertebral artery from the capillary vessel phase image of the left vertebral artery expressed as $DSA_{LVA}(i,j)$. In that situation, for example, the affine transformation unit 1e generates an inverted image expressed as $Rmask_{LVA}(i,j)$ by applying a left/right inversion to the mask image of the left vertebral artery expressed as $mask_{LVA}(i,j)$. Further, the displacement detecting unit 1f detects the displacement expressed as $(\Delta i_0, \Delta j_0)$ between $mask_{LVA}(i,j)$ and $Rmask_{LVA}(i,j)$.

Furthermore, similarly, it is also possible to generate an index image for the bloodstreams only from one of the images i.e., either an image of the right internal carotid artery or an image of the left internal carotid artery. In that situation, for example, the medical doctor presses the blood vessels positioned on the side that is not visualized using a contrast media by pressing the neck of the examined subject. As a result of the pressing, the blood pressure from the blood vessels that are being pressed becomes lower, so that the bloodstream starts flowing into the blood vessels on the opposite side, from the visualized blood vessels via the anterior communicating artery.

Further, another arrangement is acceptable in which, for example, the index image generating unit 1h generates a difference image expressed as $PF_{RICA}(i,j)$ by subtracting the inverted image expressed as $RDSA_{RICA}(i-\Delta i_0, j-\Delta j_0)$ that has been obtained by applying a left/right inversion to the capillary vessel phase image of the right internal carotid artery from the capillary vessel phase image of the right internal carotid artery expressed as $DSA_{RICA}(i,j)$. In that situation, for example, the affine transformation unit 1e generates the inverted image expressed as $Rmask_{RICA}(i,j)$ by applying a left/right inversion to the mask image of the right internal carotid artery expressed as $mask_{RICA}(i,j)$. Further, the displacement detecting unit 1f detects the displacement expressed as $(\Delta i_0, \Delta j_0)$ between $mask_{RICA}(i,j)$ and $Rmask_{RICA}(i,j)$.

Further, yet another arrangement is acceptable in which, for example, the index image generating unit 1h generates a difference image expressed as $PF_{LICA}(i,j)$ by subtracting the inverted image expressed as $RDSA_{LICA}(i-\Delta_0, j-\Delta j_0)$ that has been obtained by applying a left/right inversion to the capillary vessel phase image of the left internal carotid artery from the capillary vessel phase image of the left internal carotid artery expressed as $DSA_{LICA}(i,j)$. In that situation, for example, the affine transformation unit 1e generates the inverted image expressed as $Rmask_{LICA}(i,j)$ by applying a left/right inversion to the mask image of the left internal carotid artery expressed as $mask_{LICA}(i,j)$. Further, the displacement detecting unit 1f detects the displacement expressed as $(\Delta i_0, \Delta j_0)$ between $mask_{LICA}(i,j)$ and $Rmask_{LICA}(i,j)$.

As explained above, by using $PF_{LICA}(i,j)$ and $PF_{LICA}(i,j)$, it is possible to make a diagnosis regarding the bloodstreams into the left brain through the left internal carotid artery or regarding the bloodstreams into the right brain through the right internal carotid artery, by visualizing using a contrast media only one of the arteries i.e., either the left internal carotid artery or the right internal carotid artery. As a result, the contrast media does not have to be injected into the patient (who is the examined subject) more than once, and also, it is possible to make a diagnosis in a short period of time.

Furthermore, in the description above, the example in which each of the four major blood vessel systems in the brain is visualized using a contrast media individually is explained; however, the embodiment is not limited to this example. For example, it is acceptable to visualize using a contrast media all the four major blood vessel systems at one time through the aorta. In that situation, the affine transformation unit 1e generates an inverted image expressed as $Rmask_A(i,j)$ by applying a left/right inversion to a mask image of each of the arteries expressed as $mask_A(i,j)$. Further, the displacement detecting unit 1f detects the displacement expressed as $(\Delta i_0, \Delta j_0)$ between $mask_A(i,j)$ and $Rmask_A(i,j)$. After that, the index image generating unit 1b generates a difference image expressed as $PF_A(i,j)$ by subtracting an inverted image expressed as $RDSA_A(i-\Delta i_0, j-\Delta j_0)$ that has been obtained by applying a left/right inversion to a capillary vessel phase image of each of the arteries, from the capillary vessel phase image of the corresponding one of the arteries expressed as $DSA_A(i,j)$. With this arrangement, by injecting a contrast media to the aorta only once, it is possible to make a diagnosis to determine whether an infarction has occurred in the blood vessel systems all at one time.

The combinations of the images and the effects of the index images that have been explained above beneath Table 1 can be summarized as shown in Table 2 below. In Table 2, the images in the "mask" column and the images in the "Rmask" column are used by the displacement detecting unit 1f to detect the displacements. Further, either the image in the "DSA" column or the image in the "RDSA" column is corrected by the registration unit 1g. The images shown in the "DSA" column and the images shown in the "RDSA" column are used by the index image generating unit 1h to generate the difference images.

TABLE 2

| PF | mask | Rmask | DSA | RDSA | Effects |
|---|---|---|---|---|---|
| $PF_{LVA}(i,j)$ | $mask_{LVA}(i,j)$ | $Rmask_{LVA}(i,j)$ | $DSA_{LVA}(i,j)$ | $RDSA_{LVA}(i,j)$ | The difference in the bloodstreams through the left vertebral artery system between in the left brain and in the right brain |
| $PF_{RVA}(i,j)$ | $mask_{RVA}(i,j)$ | $Rmask_{RVA}(i,j)$ | $DSA_{RVA}(i,j)$ | $RDSA_{RVA}(i,j)$ | The difference in the bloodstreams through the right vertebral artery system between in the left brain and in the right brain |
| $PF_{RICA}(i,j)$ | $mask_{RICA}(i,j)$ | $Rmask_{RICA}(i,j)$ | $DSA_{RICA}(i,j)$ | $RDSA_{RICA}(i,j)$ | The difference in the bloodstreams in the left brain through the right internal carotid artery system from the bloodstreams in the right brain through the right internal carotid artery system (while the left internal carotid artery is being pressed) |

TABLE 2-continued

| PF | mask | Rmask | DSA | RDSA | Effects |
|---|---|---|---|---|---|
| $PF_{LICA}(i,j)$ | $mask_{LICA}(i,j)$ | $Rmask_{LICA}(i,j)$ | $DSA_{LICA}(i,j)$ | $RDSA_{LICA}(i,j)$ | The difference in the bloodstreams in the left brain through the left internal carotid artery system from the bloodstreams in the right brain through the left internal carotid artery system (while the right internal carotid artery is being pressed) |
| $PF_A(i,j)$ | $mask_A(i,j)$ | $Rmask_A(i,j)$ | $DSA_A(i,j)$ | $RDSA_A(i,j)$ | The difference between the blood streams in the left brain and in the right brain through the artery system |

As explained above, for example, the affine transformation unit 1e generates the inverted image expressed as $Rmask_{RVA}(i,j)$ obtained by applying a left/right inversion to the mask image of the right vertebral artery expressed as $mask_{RVA}(i,j)$ and generates the inverted image expressed as $RDSA_{RVA}(i,j)$ obtained by applying a left/right inversion to the capillary vessel phase image of the right vertebral artery expressed as $DSA_{RVA}(i,j)$. Further, the displacement detecting unit 1f detects the displacement expressed as $(\Delta i_0, \Delta j_0)$ between the mask image of the right vertebral artery expressed as $mask_{RVA}(i,j)$ and the inverted image expressed as $Rmask_{RVA}(i,j)$. Further, the registration unit 1g generates the corrected inverted image expressed as $RDSA_{RVA}(i-\Delta i_0, j-\Delta j_0)$ obtained by correcting the inverted image expressed as $RDSA_{RVA}(i,j)$, based on the detected displacement expressed as $(\Delta i_0, \Delta j_0)$. After that, the index image generating unit 1h generates the difference image expressed as $PF_{RVA}(i,j)$ between the capillary vessel phase image of the right vertebral artery expressed as $DSA_{RVA}(i,j)$ and the inverted image expressed as $RDSA_{RVA}(i-\Delta i_0, j-\Delta j_0)$, as the index image indicating an index for the bloodstreams.

Alternatively, another arrangement is acceptable in which the registration unit 1g generates a corrected image expressed as $DSA_{RVA}(i+\Delta i_0, j+\Delta j_0)$ obtained by correcting the capillary vessel phase image of the right vertebral artery expressed as $DSA_{RVA}(i,j)$, based on the displacement expressed as $(\Delta i_0, \Delta j_0)$ that has been detected by the displacement detecting unit 1f. In that situation, the index image generating unit 1h generates a difference image between the corrected image expressed as $DSA_{RVA}(i+\Delta i_0, j+\Delta j_0)$ and the inverted image expressed as $RDSA_{RVA}(i,j)$, as $PF_{RVA}(i,j)$.

With the configuration described above, it is possible to reduce the burden on the patient who is the examined subject, because it is possible to obtain the index image indicating an index for the bloodstreams by visualizing using a contrast media only one blood vessel. In addition, it is also possible to shorten the time period it takes to make the diagnosis.

In the description of the first embodiment above, the example is explained in which the capillary vessel phase image is generated by calculating the arithmetic average of the capillary vessel phase frames that have been identified out of the plurality of DSA images taken in a time sequence so that the difference image between the capillary vessel phase image and the inverted image obtained by applying an inversion to the capillary vessel phase image is generated. In other words, according to the first embodiment, the capillary vessel phase image and the inverted image being used are taken at mutually the same point in time at which a certain period of time has elapsed since the contrast media was injected into the examined subject.

However, in the case where, for example, an infarction has occurred either in a blood vessel positioned on the right side of the brain or in a blood vessels positioned on the left side of the brain, there is a possibility that the point in time at which the blood vessels positioned on the right side are visualized using a contrast media may be different from the point in time at which the blood vessels positioned on the left side are visualized using a contrast media. To cope with this situation, an arrangement is acceptable in which, for example, a difference image is generated after the time difference between the left and the right is corrected based on profiles related to contrast media densities. In the following sections, an example in which the time difference between the left and the right is corrected will be explained as a second embodiment.

In the second embodiment, the subtraction unit 1d generates a plurality of DSA images of the right internal carotid artery expressed as $DSA_{RICAn}(i,j)$ by generating a difference image between each of a plurality of contrast images expressed as $contrast_{RICAn}(i,j)$ that have sequentially been taken after the right internal carotid artery is visualized using a contrast media and the mask image of the right internal carotid artery expressed as $mask_{RICA}(i,j)$. Also, the subtraction unit 1d generates a plurality of DSA images of the left internal carotid artery expressed as $DSA_{LICAn}(i,j)$ by generating a difference image between each of a plurality of contrast images expressed as $contrast_{LICAn}(i,j)$ that have sequentially been taken after the left internal carotid artery is visualized using a contrast media and the mask image of the left internal carotid artery, expressed as $mask_{LICA}(i,j)$.

Further, the affine transformation unit 1e generates an inverted image expressed as $Rmask_{RICA}(i,j)$ obtained by applying a left/right inversion to $mask_{RICA}(i,j)$ and generates a plurality of inverted images expressed as $RDSA_{RICAn}(i,j)$ obtained by inverting the plurality of images expressed as $DSA_{RICAn}(i,j)$ that have been generated by the subtraction unit 1d. Further, in the same manner as in the first embodiment, the displacement detecting unit 1f detects a displacement between $mask_{LICA}(i,j)$ and $Rmask_{RICA}(i,j)$.

Further, based on the displacement that has been detected by the displacement detecting unit 1f, the registration unit 1g generates a plurality of corrected images expressed as $DSA_{LICAn}(i-\Delta i_0, j-\Delta j_0)$ that are obtained by correcting the plurality of images expressed as $DSA_{LICAn}(i,j)$ that have been generated by the subtraction unit 1d. Alternatively, another arrangement is acceptable in which the registration unit 1g generates a plurality of corrected inverted images expressed as $RDSA_{RICAn}(i+\Delta i_0, j+\Delta j_0)$ that are obtained by correcting the plurality of images expressed as $RDSA_{RICAn}(i,j)$ that have been generated by the affine transformation unit 1e.

Further, with respect to an image group made up of the plurality of images expressed as $RDSA_{RICAn}(i,j)$ that have been generated by the affine transformation unit $1e$ and another image group made up of the plurality of images expressed as $DSA_{RICAn}(i-\Delta i_0, j-\Delta j_0)$ that have been generated by the registration unit $1g$, the index image generating unit $1h$ generates a difference image between these two image groups after correcting, for each set of pixels in mutually the same position, a time difference between a temporal change in the contrast media density in one of the image groups and a temporal change in the contrast media density in the other of the image groups. Alternatively, another arrangement is acceptable in which, with respect to an image group made up of the plurality of images expressed as $DSA_{LICAn}(i,j)$ that have been generated by the subtraction unit $1d$ and another image group made up of the plurality of images expressed as $RDSA_{RICAn}(i-\Delta i_0, j-\Delta j_0)$ that have been generated by the registration unit $1g$, the index image generating unit $1h$ generates a difference image between these two image groups after correcting a time difference for each set of pixels in mutually the same position.

Figure 5:
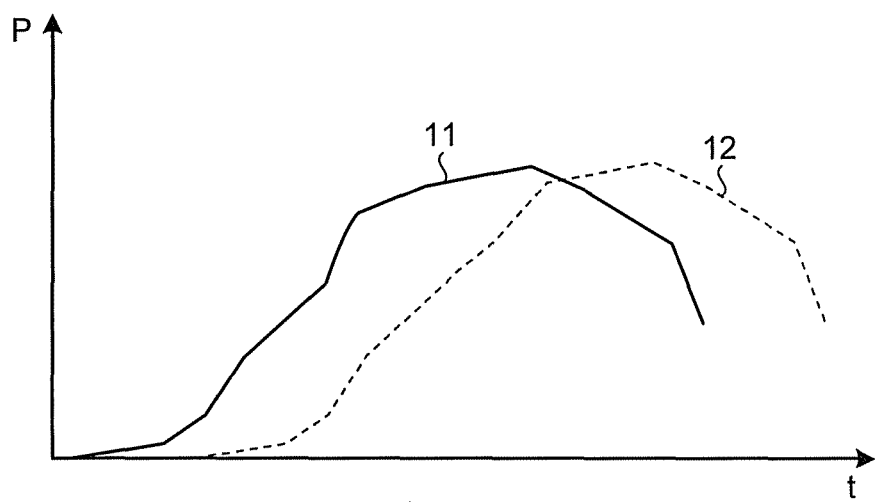
FIGS. 5 to 7 are charts for explaining a time difference correcting process and a difference image generating process that are performed by an index image generating unit 1h according to a second embodiment.
Figure 6:
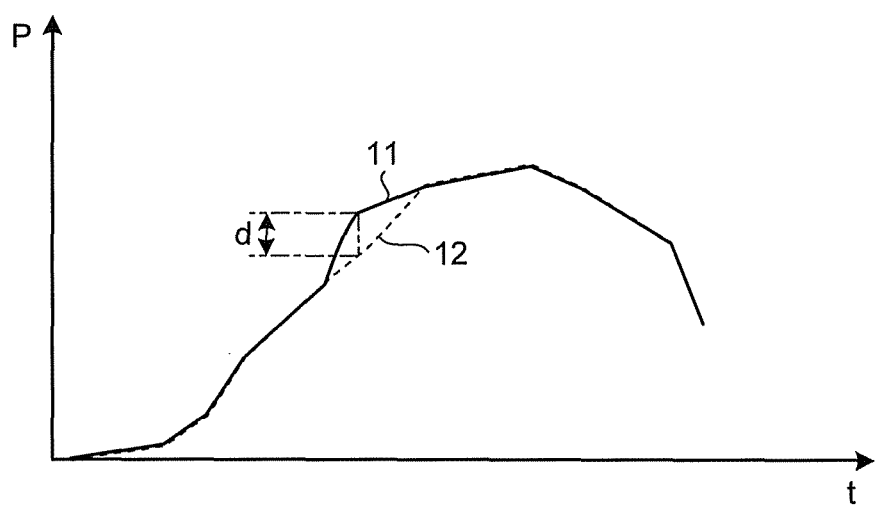
Figure 7:
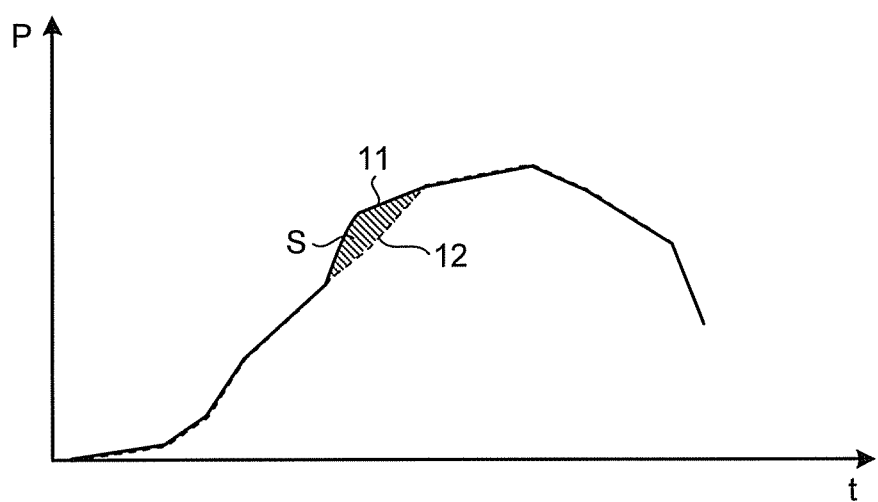

FIGS. 5 to 7 are charts for explaining a time difference correcting process and a difference image generating process that are performed by the index image generating unit $1h$ according to the second embodiment. In FIGS. 5 to 7, the vertical axis P expresses a contrast media density, whereas the horizontal axis t expresses an elapsed time period since a contrast media is injected into an examined subject. A curve 11 drawn with a solid line expresses a temporal change in the contrast media density in an image group made up of the images expressed as $RDSA_{RICAn}(i,j)$. Further, a curve 12 drawn with a broken line expresses a temporal change in the contrast media density in an image group made up of the images expressed as $DSA_{LICAn}(i-\Delta i_0, j-\Delta j_0)$. The curve 11 and the curve 12 express the changes in the contrast media densities in positions that are bilaterally symmetric to each other in the brain. For example, in the case where an infarction has occurred in a blood vessel supplying blood to the left internal carotid artery, the left internal carotid artery is visualized using a contrast media later than the right internal carotid artery, as shown in FIG. 5.

In that situation, the index image generating unit $1h$ corrects the times of either $RDSA_{RICAn}(i,j)$ or $DSA_{LICAn}(i-\Delta i_0, j-\Delta j_0)$ in such a manner that the difference between the curve 11 and the curve 12 becomes smallest in a ROI which has predetermined size at center of image. For example, the index image generating unit $1h$ performs a correcting process to change the times of $DSA_{LICAn}(i-\Delta i_0, j-\Delta j_0)$ in such a manner that the difference between the curve 11 and the curve 12 becomes smallest in the ROI, as shown in FIG. 6. For example, in the situation where the time of each of the images $RDSA_{RICAn}(i,j)$ is expressed as $t_0$ whereas the time of each of the images $DSA_{LICAn}(i-\Delta i_0, j-\Delta j_0)$ is expressed as $t_0-\Delta t$, the index image generating unit $1h$ calculates the degree of correlation between the curve 11 and the curve 12 while varying the value of $\Delta t$. Further, by identifying such a value of $\Delta t$ that makes the degree of correlation between the curve 11 and the curve 12 highest, the index image generating unit $1h$ corrects the times of $DSA_{LICAn}(i-\Delta i_0, j-\Delta j_0)$. A value of $\Delta t$ is determined with maximum frequency of $\Delta t$ in the ROI. Alternatively, the index image generating unit $1h$ may correct the times of $RDSA_{RICAn}(i,j)$.

After that, the index image generating unit $1h$ extracts, for each set of pixels in mutually the same position, the maximum value among the differences between the contrast media densities in one of the image groups and the contrast media densities in the other of the image groups and generates a difference image by using the extracted maximum values. For example, as shown in FIG. 6, after correcting the times of $DSA_{LICAn}(i-\Delta i_0, j-\Delta j_0)$ in such a manner that the difference between the curve 11 and the curve 12 becomes smallest, the index image generating unit $1h$ calculates, for each set of pixels in mutually the same position, a difference in the contrast media densities between $RDSA_{RICAn}(i,j)$ and $DSA_{LICAn}(i-\Delta i_0, j-\Delta j_0)$. After that, the index image generating unit $1h$ generates a difference image by using a maximum value d among the contrast media densities that has been calculated for each of the pixels. As a result, it is possible to obtain the difference image in which the part that has a large difference in the contrast media density between the left and the right is emphasized.

Alternatively, another arrangement is acceptable in which the index image generating unit $1h$ calculates, for each set of pixels in mutually the same position, a total sum of the differences between the contrast media densities in one of the image groups and the contrast media densities in the other of the image groups and generates a difference image by using the calculated total sums. For example, as shown in FIG. 7, after correcting the times of $DSA_{LICAn}(i-\Delta i_0, j-\Delta j_0)$ in such a manner that the difference between the curve 11 and the curve 12 becomes smallest, the index image generating unit $1h$ calculates, for each set of pixels in mutually the same position, a total sum S of differences in the contrast media densities between $RDSA_{RICAn}(i,j)$ and $DSA_{LICAn}(i-\Delta i_0, j-\Delta j_0)$. Subsequently, the index image generating unit $1h$ generates a difference image by using the total sum S of the differences in the contrast media densities that has been calculated for each of the pixels. As a result, it is possible to obtain the difference image in which the part that has a large difference in the contrast media density between the left and the right is emphasized.

Alternatively, another arrangement is acceptable in which, with respect to an image group made up of the plurality of images expressed as $DSA_{LICAn}(i,j)$ and another image group made up of the plurality of images expressed as $RDSA_{RICAn}(i,j)$, the index image generating unit $1h$ generates a difference image between these two image groups after correcting the time difference between these two image groups.

As explained above, according to the second embodiment, the difference image is generated after the time difference between the left and the right is corrected based on the profiles related to the contrast media densities, it is possible to render a lesion area of the examined subject in a medical image, with a higher level of precision. In the description above, the example in which the time difference between the left and the right is corrected based on the profiles related to the contrast media densities is explained; however, another arrangement is acceptable in which, for example, the time difference between the left and the right is corrected based on profiles related to speeds at which the contrast media densities change.

In the description of the second embodiment above, the example is explained in which, as shown in FIGS. 6 and 7, the contrast media densities on the left and on the right change in such a manner that the curve 11 and the curve 12 intersect each other in the latter half portion where the contrast media densities become lower; however, there may be a situation in which the curve 11 and the curve 12 do not intersect each other in the latter half portion, if the time period of visualizing using a contrast media is significantly different between the left and the right. In that situation, another arrangement is acceptable in which, for example, after correcting the time differences of the images in such a manner that the difference between the curve 11 and the curve 12 becomes smallest, the index image generating unit $1h$ calculates either the maximum value d or the total sum S of the differences in the contrast media densities in the time period before one of the curves reaches a peak.

Furthermore, in the description of the second embodiment above, the example in which the DSA images of both the right internal carotid artery and the left internal carotid artery are used is explained. It is, however, possible to similarly implement the second embodiment described above by, for example, using the DSA images of either the right internal carotid artery or the left internal carotid artery, or using the DSA images of one or both of the right vertebral artery and the left vertebral artery.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
   an image inverting unit obtaining a masking image for a first medical image that generates a first inverted image obtained by inverting the first medical image in a left-and-right direction of an examined subject and generates a second inverted image obtained by inverting a second medical image that is different from the first medical image in the left-and-right direction of the examined subject;
   a displacement detecting unit that detects a displacement between the first medical image and the first inverted image;
   a registration unit that, based on the displacement that has been detected by the displacement detecting unit, generates one of a corrected image obtained by correcting the second medical image and a corrected inverted image obtained by correcting the second inverted image; and
   a difference image generating unit that generates one of a difference image between the second inverted image and the corrected image and a difference image between the second medical image and the corrected inverted image.

2. The medical image processing apparatus according to claim 1, wherein
   the first medical image is an X-ray image taken before a blood vessel is visualized using a contrast media, and
   the second medical image is a difference image that has been generated from an X-ray image taken after the blood vessel is visualized using a contrast media and the first medical image.

3. The medical image processing apparatus according to claim 2, further comprising: a medical image generating unit that generates a plurality of second medical images by generating a difference image between each of a plurality of X-ray images that are sequentially taken after the blood vessel is visualized using a contrast media and the first medical image, wherein
   the image inverting unit generates the first inverted image and a plurality of second inverted images that are obtained by inverting the plurality of second medical images,
   the registration unit, based on the displacement that has been detected by the displacement detecting unit, generates one of the following: a plurality of corrected images obtained by correcting the plurality of second medical images; and a plurality of corrected inverted images obtained by correcting the plurality of second inverted images, and
   the difference image generating unit generates, either with respect to one image group made up of the plurality of second inverted images and another image group made of up the plurality of corrected images or with respect to one image group made up of the plurality of second medical images and another image group made up of the plurality of corrected inverted images, a difference image between the one image group and said another image group after correcting, for each set of pixels in a mutually same position, a time difference between a temporal change in a contrast media density in the one image group and a temporal change in a contrast media density in said another image group.

4. The medical image processing apparatus according to claim 3, wherein the difference image generating unit extracts, for each set of pixels in a mutually same position, a maximum value among differences between contrast media densities in the one image group and contrast media densities in said another image group and generates the difference image by using the extracted maximum values.

5. The medical image processing apparatus according to claim 3, wherein the difference image generating unit calculates, for each set of pixels in a mutually same position, a total sum of differences between contrast media densities in the one image group and contrast media densities in said another image group and generates the difference image by using the calculated total sums.

6. The medical image processing apparatus according to claim 1, wherein the medical image processing apparatus includes a X-ray computer tomography (CT) device and a magnetic resonance imaging (MRI) device.

7. A medical image processing apparatus comprising:
   an image inverting unit obtaining a masking image for a first medical image that generates a first inverted image obtained by inverting the first medical image in a left-and-right direction of an examined subject and generates a second inverted image obtained by inverting, in the left-and-right direction of the examined subject, a second medical image that is taken by performing a procedure that forms a series of procedures together with a procedure for taking the first medical image;
   a displacement detecting unit that detects a displacement between a third medical image that is different from the first medical image and the first inverted image;
   a registration unit that, based on the displacement that has been detected by the displacement detecting unit, generates one of the following: a corrected image obtained by correcting a fourth medical image that is taken by performing a procedure that forms a series of procedures together with a procedure for taking the third medical image;
   and a corrected inverted image obtained by correcting the second inverted image; and
   a difference image generating unit that generates one of a difference image between the second inverted image and the corrected image and a difference image between the fourth medical image and the corrected inverted image.

8. The medical image processing apparatus according to claim 7, wherein
   the first medical image is an X-ray image taken before a first blood vessel is visualized using a contrast media, the second, medical image is a difference image that has been generated from an X-ray image taken after the first blood vessel is visualized using a contrast media and the first medical image, the third medical image is an X-ray image taken before a second blood vessel that is different from the first blood vessel is visualized using a contrast media, and the fourth medical image is a difference image that has been generated from an X-ray image taken after the second blood vessel is visualized using a contrast media and the third medical image.

9. The medical image processing apparatus according to claim 8, further comprising: a medical image generating unit that generates a plurality of second medical images by generating a difference image between each of a plurality of X-ray images that are sequentially taken after the first blood vessel is visualized using a contrast media and the first medical image and generates a plurality of fourth medical images by generating a difference image between each of a plurality of X-ray images that are sequentially taken after the second blood vessel is visualized using a contrast media and the third medical image, wherein the image inverting unit generates the first inverted image and a plurality of second inverted images that are obtained by inverting the plurality of second medical images, the registration unit, based on the displacement that has been detected by the displacement detecting unit, generates one of the following: a plurality of corrected images obtained by correcting the plurality of fourth medical images; and a plurality of corrected inverted images obtained by correcting the plurality of second inverted images, and the difference image generating unit generates, either with respect to one image group made up of the plurality of second inverted images and another image group made of up the plurality of corrected images or with respect to one image group made up of the plurality of fourth medical images and another image group made up of the plurality of corrected inverted images, a difference image between the one image group and said another image group after correcting, for each set of pixels in a mutually same position, a time difference between a temporal change in a contrast media density in the one image group and a temporal change in a contrast media density in said another image group.

10. The medical image processing apparatus according to claim 9, wherein the difference image generating unit extracts, for each set of pixels in a mutually same position, a maximum value among differences between contrast media densities in the one image group and contrast media densities in said another image group and generates the difference image by using the extracted maximum values.

11. The medical image processing apparatus according to claim 9, wherein the difference image generating unit calculates, for each set of pixels in a mutually same position, a total sum of differences between contrast media densities in the one image group and contrast media densities in said another image group and generates the difference image by using the calculated total sums.

12. The medical image processing apparatus according to claim 7, wherein the medical image processing apparatus includes a X-ray computer tomography (CT) device and a magnetic resonance imaging (MRI) device.

13. A medical image processing method comprising:
obtaining a masking image for a first medical image and generating a first inverted image obtained by inverting the first medical image in a left-and-right direction of an examine subject and generating a second inverted image obtained by inverting, in the left-and-right direction of the examined subject, a second medical image that is taken by performing a procedure that forms a series of procedures together with a procedure for taking the first medical image;

detecting a displacement between a third medical image that is different from the first medical image and the first inverted image; generating, based on the displacement that has been detected, one of the following: a corrected image obtained by correcting a fourth medical image that is taken by performing a procedure that forms a series of procedures together with a procedure for taking the third medical image;

and a corrected inverted image obtained by correcting the second inverted image; and generating one of a difference image between the second inverted image and the corrected image and a difference image between the fourth medical image and the corrected inverted image.

14. The medical image processing apparatus according to claim 13, wherein the medical image processing apparatus includes a X-ray computer tomography (CT) device and a magnetic resonance imaging (MRI) device.

15. A medical image processing method comprising:
obtaining a masking image for a first medical image and generating a first inverted image obtained by inverting the first medical image in a left-and-right direction of an examined subject and generating a second inverted image obtained by inverting, in the left-and-right direction of the examined subject, a second medical image that is taken by performing a procedure that forms a series of procedures together with a procedure for taking the first medical image;

detecting a displacement between a third medical image that is different from the first medical image and the first inverted image;

generating, based on the displacement that has been detected, one of the following: a corrected image obtained by correcting a fourth medical image that is taken by performing a procedure that forms a series of procedures together with a procedure for taking the third medical image; and a corrected inverted image obtained by correcting the second inverted image ; and generating one of a difference image between the second inverted image and the corrected image and a difference image between the fourth medical image and the corrected inverted image.

16. The medical image processing apparatus according to claim 15, wherein the medical image processing apparatus includes a X-ray computer tomography (CT) device and a magnetic resonance imaging (MRI) device.

* * * * *